United States Patent [19]

Yokomori et al.

[11] Patent Number: 5,089,654
[45] Date of Patent: Feb. 18, 1992

[54] CHALCONE DERIVATIVES

[75] Inventors: Sadakazu Yokomori, Urawa; Keiko Saijo, Saitama; Tohru Matsunaga, Kuki; Yoshimoto Nakashima, Ageo; Katsuo Hatayama, Omiya, all of Japan

[73] Assignee: Taisho Pharmaceutical Co., Ltd., Japan

[21] Appl. No.: 562,602

[22] Filed: Aug. 3, 1990

[30] Foreign Application Priority Data

Aug. 8, 1989 [JP] Japan .................. 1-205005

[51] Int. Cl.$^5$ .................. C07C 69/76
[52] U.S. Cl. .................. 560/53; 562/460; 562/463
[58] Field of Search .................. 560/53; 562/463

[56] References Cited

U.S. PATENT DOCUMENTS 4,085,135 4/1978 Kyogoku et al. .................. 260/520
4,656,305 4/1987 Vanstone et al. .................. 560/64

FOREIGN PATENT DOCUMENTS 51-14578 2/1976 Japan .
56-84452 11/1981 Japan .
184453 11/1981 Japan .
57-203585 12/1981 Japan .
848836 1/1982 Japan .

OTHER PUBLICATIONS

Chemical Abstracts, vol. 99, No. 15, 10/10/83, p. 614, col. 1, No. 122052h.
Chemical Abstracts, vol. 99, No. 15, 12/83, p. 721, col. 1, No. 194622s.
Chemical Abstracts, vol. 100, No. 3, 1/16/84, p. 469, col. 2, No. 22418c.

*Primary Examiner*—Paul J. Killos
*Attorney, Agent, or Firm*—Lorusso & Loud

[57] ABSTRACT

Chalcone derivatives represented by the formula

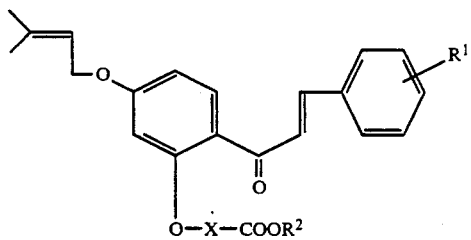

wherein $R^1$ is a straight chain, branched chain or cyclic alkyl group having 4 to 15 carbon atoms or an alkenyl group having 3 to 15 carbon atoms, and occurs at the 2- or 4-position, $R^2$ is a hydrogen atom, a straight or branched chain alkyl group having 1 to 3 carbon atoms, and X is a straight or branched chain alkylene group having 1 to 3 carbon atoms, are disclosed. These compounds have anti-ulcer effect, gastric mucosal protection effect and antisecretory effect.

8 Claims, No Drawings

CHALCONE DERIVATIVES

BACKGROUND OF THE INVENTION

(1) Field of the Invention

The present invention relates to novel chalcone derivatives substituted by an alkyl or alkenyl group having a proper number of carbon atoms at the 2- or 4-position of the chalcone skeleton and intermediates for preparing the same, and more particularly novel chalcone delivatives having anti-ulcer effect and gastric mucosa protection effect for the treatment of gastric diseases, and the intermediates for preparing the same.

(2) Related Art

At present $H_2$ receptor antagonists take the lead of the primary choice drugs for the treatment of gastric and duodenal ulcers because of their high healing rate and rapid remission of diseases. However, in the pharmacotherapy using $H_2$ receptor antagonists, there are remained serious problems to solve, such as side-effects (e.g., hypergastrinemia) and the relapse of the disease in high frequency after discontinuation of the medication.

In order to solve such problems, beginning with an isoprenylchalcone compound known by the general name of "sofalcone" in U.S. Pat. No. 4,085,135, some carboxyalkoxychalcone derivatives have been disclosed as the compounds having the anti-ulcer effect (e.g., See U.S. Pat. No. 4,656,305). However, there is a need for the development of the protective-type drug having strong anti-ulcer effect which can be a primary choice drug for the treatment of ulcer.

The present inventors have found that the 2'-carboxyalkoxychalcone compounds with an alkyl or alkenyl group having proper numbers of carbon atoms at the 2- or 4-position have more excellent anti-ulcer effect, gastric mocosa protection effect and antisecretory effect than the known carboxyalkoxychalcone derivatives, have added the further research to the finding, and have accompleshed the present invention.

SUMMARY OF THE INVENTION

An object of the invention is to provide a chalcone derivative represented by the formula

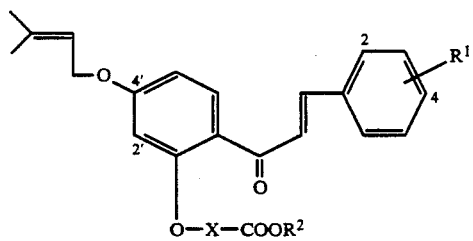

(I)

wherein $R^1$ is a straight chain, branched chain or cyclic alkyl group having 4 to 15 carbon atoms or an alkenyl group having 3 to 15 carbon atoms, and occurs at the 2- or 4-position, $R^2$ is a hydrogen atom, a straight or branched chain alkyl group having 1 to 3 carbon atoms, and X is a straight or branched chain alkylene group having 1 to 3 carbon atoms.

Another object of the present invention is to provide a 2'-hydroxychalcone derivative represented by the formula

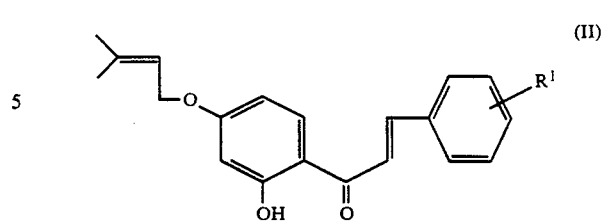

(II)

wherein $R^1$ is a straight chain, branched chain or cyclic alkyl group having 4 to 15 carbon atoms or an alkenyl group having 3 to 15 carbon atoms, and occurs at the 2- or 4-position.

DETAILED DESCRIPTION OF THE INVENTION

In the specification, $R^1$ is a straight chain, branched chain or cyclic alkyl group having 4 to 15 carbon atoms and occurs at the 2- or 4-position, or alkenyl group having 3 to 15 carbon atoms, and occurs at the 2- or 4-position. $R^1$ is preferably a straight chain alkyl group having 5 to 8 carbon atoms, a branched chain alkyl group having 4 to 7 carbon atoms, or an alkenyl group having 4 to 8. And $R^1$ is most preferably a straight chain having 6 or 7 carbon atoms, a 1-alkenyl group having 6 or 7 carbon atoms or a branched chain alkyl group having 4 carbon atoms, and occurs at the 4-position.

$R^2$ is a hydrogen atom, or the straight or branched chain alkyl group having 1 to 3 carbon atoms, and preferably hydrogen atom, a methyl group, an ethyl group or a n-propyl group. And $R^2$ is most preferably a hydrogen atom.

X is a straight or branched chain alkylene group having 1 to 3 carbon atoms, and preferably a methylene group.

A preparation of the compounds of the present invention is illustrated below, and the outline is given by the following Reaction Scheme I.

Reaction Scheme I

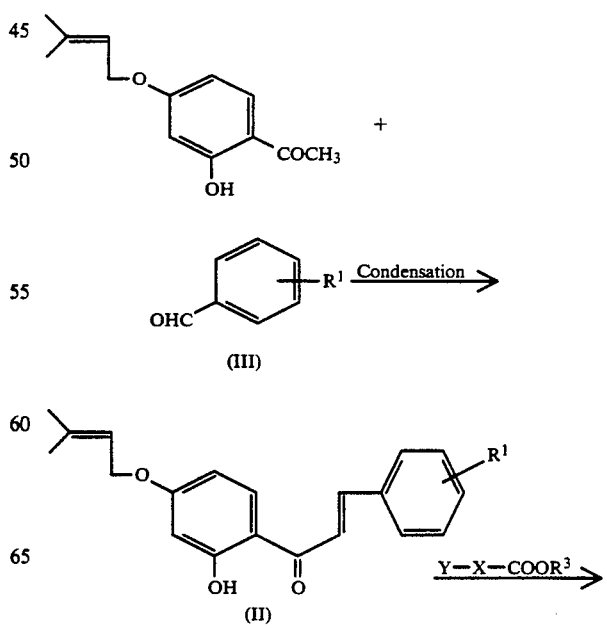

-continued
Reaction Scheme I

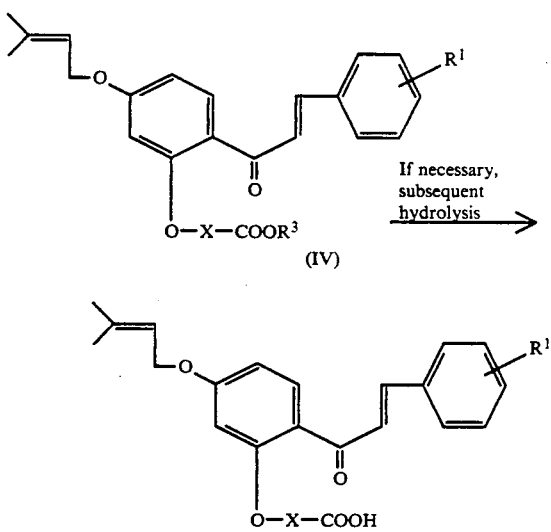

First, 2'-hydroxy-4'-(3-methyl-2-butenyloxy)-acetophenone is condensed with a benzaldehyde represented by the formula

(III)

wherein $R^1$ and the position thereof are as defined above, which can be prepared by a method as described in J. Org. Chem., vol. 49, page 3963 (1984) or Syn. Commun., vol. 13, page 177 (1983), in the presence of an alkali in a solvent to give a 2'-hydroxychalcone derivative of Formula II.

Examples of the alkali used in the condensation are potassium hydroxide, sodium hydroxide, sodium ethoxide, sodium methoxide, potassium t-butoxide, potassium carbonate, sodium carbonate, sodium bicarbonate and potassium bicarbonate. As the reaction solvents, for example, methanol, ethanol, n-propanol, isopropanol and t-butanol can be used alone or in combination with water. The reaction temperature can be properly chosen from the range of 0° C. to the boiling point of the solvent used.

Then, a 2'-hydroxychalcone derivative of Formula II is reacted with a compound represented by the formula

Y-X-COOR³        (IV)

(wherein $R^3$ is an alkyl group having 1 to 3 carbon atoms, X is as defined above, and Y is a chlorine atom, a bromine atom, an iodine atom, a mesyl group or a tosyl group), in the presence of a base in a solvent to give a compound of Formula I wherein $R^2$ is other than a hydrogen atom.

Examples of the base used in the reaction are potassium carbonate, sodium carbonate, sodium bicarbonate, potassium bicarbonate, potassium hydroxide, sodium hydroxide, sodium hydride, potassium hydride, sodium ethoxide, sodium methoxide, sodium amide, potassium amide, n-butyl lithium, lithium diisopropylamide and potassium t-butoxide. Examples of the reaction solvent used are methanol, ethanol, n-propanol, isopropanol, acetone, dimethylformamide, dimethyl sulfoxide, benzene, toluene, tetrahydrofuran, dioxane, acetonitrile, chloroform and dichloromethane. A phase transfer catalyst or an iodide compound (e.g., potassium iodide and sodium iodide) may be used as a reaction accelerator. The reaction temperature can be properly chosen from a range of −70° C. to the boiling point of the solvent used.

The compound of Formula I wherein $R^2$ is a hydrogen atom can be prepared by hydrolysis of the compound of Formula I wherein $R^2$ is other than a hydrogen atom.

The hydrolysis can be carried out using an aqueous solution of an alkali such as potassium carbonate, sodium carbonate, sodium bicarbonate, potassium bicarbonate, potassium hydroxide and sodium hydroxide in a solvent such as an alcohol (e.g., methanol, ethanol, n-propanol and isopropanol), tetrahydrofuran and dioxane at a temperature of from 0° C. to the boiling point of the solvent used.

The compound of Formula I can be also prepared by a reaction of a compound represented by the formula

Y'-X-COOH        (V)

(wherein X is as defined above, and Y' is a chlorine atom, a bromine atom, an iodine atom, a mesyl group or a tosyl group) or an alkali salt thereof with a 2'-hydroxychalcone derivative of Formula II.

An alternative preparation of the compound of the present invention is presented generally by the following Reaction Scheme II.

Reaction Scheme II

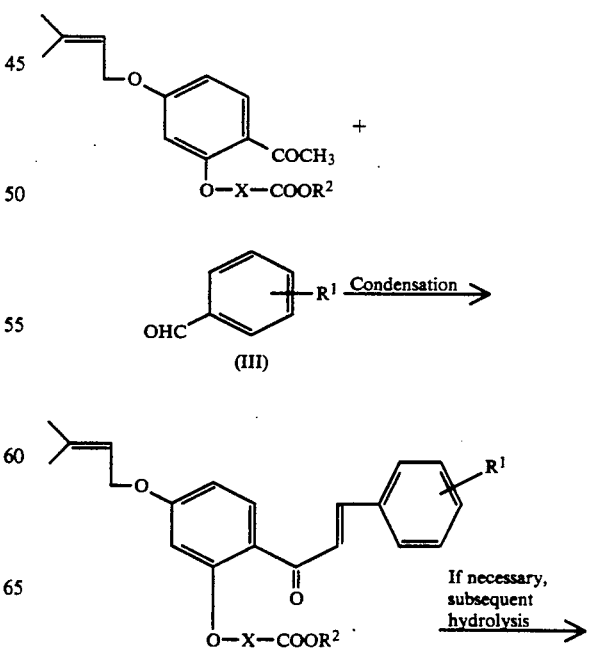

-continued
Reaction Scheme II

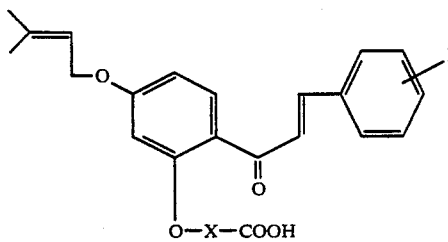

wherein $R^1$ and $R^2$ are as defined above; and the reaction conditions in each step are the same as the corresponding steps of Reaction Scheme I.

The compounds of Formula I of the present invention have a potent anti-ulcer effect, gastric mucosa protection effect, antisecretory effect, and therefore, they are useful for the treatment or prevention of gastric inflammatory diseases (e.g., gastritis), gastric ulcer and duodenal ulcer. For the purpose, these compounds can be administered orally or parenterally in a conventional dosage form such as tablets, powders, granules, emulsions, suspensions and solutions, each of which can be prepared by conventional pharmaceutical practices.

The daily dosage of the compound of Formula I in adult human may be from about 10 to 1200 mg per day in one to three divided doses.

The compounds of Formula I have low toxicity. The $LD_{50}$ value in the case of oral administration is more than 2,000 mg/kg in mice.

The compounds of Formula II are useful as intermediates for preparing the compounds of Formula I.

The present invention is illustrated in more detail by the following examples and experiments.

Example 1

Preparation of
4-n-hexyl-2'-hydroxy-4'-(3-methyl-2-butenyloxy)chalcone

To a solution of 6.60 g of 2'-hydroxy-4'-(3-methyl-2-butenyloxy)acetophenon and 5.70 g of 4-n-hexylbenzaldehyde in 120 ml of isopropyl alcohol was added 25 ml of 6 N sodium hydroxide aqueous solution, and the reaction was carried out at 40° C. for 8 hours. After completion of the reaction, the reaction mixture was neutralized with dilute hydrochloric acid. The precipitated solid was collected by filtration, washed with water, dried and recrystallized from ethanol to give 7.72 g of 4-n-hexyl-2'-hydroxy-4'-(3-methyl-2-butenyloxy)-chalcone as yellow needles.

m.p. 74°–75° C.

MS m/z: 392(M+), 324, 69

$IR\nu_{max}^{KBr}$ cm$^{-1}$: 3440(OH), 2927, 1642(C=O)

PMR (DMSO-d$_6$) δ: 0.86(3H, t, J=7 Hz), 1.28(6H, m), 1.52–1.65(2H, m), 1.73(3H, s), 1.76(3H, s), 2.62(2H, t, J=8 Hz), 4.63(2H, d, J=7 Hz), 5.44(1H, t, J=7 Hz), 6.51–6.58(2H, m), 7.29(2H, d, J=8 Hz), 7.76–7.84(3H, m), 7.97(1H, d, J=15 Hz), 8.27(1H, d, J=9 Hz), 13.50(1H, s).

Examples 2 to 11

In a similar manner to that of Example 1, the compounds shown in Table 1 were obtained.

TABLE 1

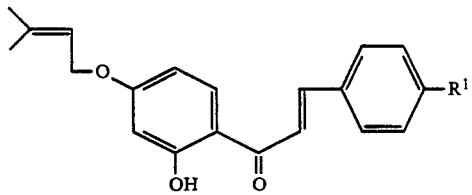

| Example | $R^1$ | m.p. (°C.) (Solvent for recrystallization) | Appearance | Reaction conditions | Yield (%) |
|---|---|---|---|---|---|
| 2 | n-C$_4$H$_9$ | 84–85 (EtOH) | Yellow needles | aqKOH/EtOH | 59.7 |
| 3 | iso-C$_4$H$_9$ | 82–83 (EtOH | Yellow plates | aqKOH/EtOH | 63.8 |
| 4 | n-C$_5$H$_{11}$ | 88–89 (EtOH) | Yellow needles | aqNaOH/EtOH | 58.3 |
| 5 | iso-C$_5$H$_{11}$ | 77–79 (EtOH) | Yellow needles | aqNaOH/EtOH | 53.5 |
| 6 | n-C$_6$H$_{13}$ | 74–75 (EtOH) | Yellow needles | aqKOH/EtOH | 62.9 |
| 7 | n-C$_7$H$_{15}$ | 83–84 (EtOH) | Yellow needles | aqKOH/EtOH | 52.1 |
| 8 | n-C$_8$H$_{17}$ | 76–77 (EtOH) | Yellow needles | aqKOH/EtOH | 59.6 |
| 9 | n-C$_{10}$H$_{21}$ | 82–83 (EtOH) | Yellow powder | aqKOH/IPA | 53.7 |
| 10 | sec-C$_4$H$_9$ | 34–37 (IPA) | Yellow powder | KOH/EtOH | 45.3 |
| 11 | cyclo-C$_6$H$_{11}$ | 118–119 (EtOH) | Yellow needles | aqKOH/EtOH | 32.3 |

Example 12

Preparation of
2'-ethoxycarbonylmethoxy-4-n-hexyl-4'-(3-methyl-2-butenyloxy)chalcone To a solution of 5.50 g of 4-n-hexyl-2'-hydroxy-4'-(3-methyl-2-butenyloxy)chalcone in 55 ml of dry acetone was added 1.4 g of crushed potassium hydroxide. After stirring for 5 minutes, 2.40 g of ethyl bromoacetate was added, and the mixture was stirred at room temperature for 40 minutes. After completion of the reaction, the reaction mixture was neutralized by adding dropwise dilute hydrochloric acid with ice cooling. The precipitated solid was collected by filtration, washed with water, dried and recrystallized from ethanol to give 5.73 g of 2'-ethoxycarbonylmethoxy-4-n-hexyl-4'-(3-methyl-2-butenyloxy)chalcone as pale yellow needles.

m.p. 56°–57° C.

MS m/z: 478(M+), 410, 69

$IR\nu_{max}^{KBr}$ cm$^{-1}$: 2976, 2929, 1763(C=O), 1645(C=O), 1608, 1578, 1218, 1185.

PMR(DMSO-d$_6$) δ: 0.85(3H, t, J=7 Hz), 1.19(3H, t, J=7 Hz), 1.21–1.31(6H, m), 1.53–1.60(2H, m), 1.73(3H, s), 1.76(3H, s), 2.60(2H, t, J=8 Hz), 4.19(2H, q, J=7 Hz), 4.61(2H, d, J=7 Hz), 5.00(2H, s), 5.45(1H, t, J=7

Hz), 6.65-6.70(2H, m), 7.25(2H, d, J=8 Hz), 7.54-7.68(4H, m), 7.84(1H, d, J=16 Hz).

Examples 13 to 22

In a similar manner to that of Example 12, the compounds shown in Table 2 were obtained.

TABLE 2

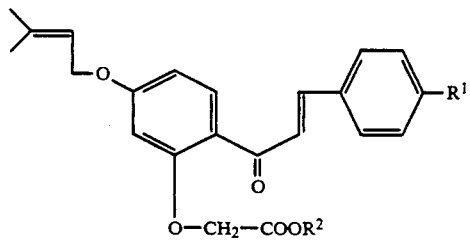

| Example | $R^1$ | $R^2$ | m.p. (°C) (Solvent for recrystallization) | Appearance | Reaction conditions | Yield (%) |
|---|---|---|---|---|---|---|
| 13 | n-$C_4H_9$ | $CH_3$ | 54-55 (EtOH) | Pale yellow needles | NaH/DMF | 62.6 |
| 14 | iso-$C_4H_9$ | $CH_3$ | 67-69 (EtOH) | Pale Yellow plates | KOH/acetone | 73.3 |
| 15 | iso-$C_5H_{11}$ | $C_2H_5$ | 50-52 (EtOH) | Pale yellow needles | KH/DMF | 73.4 |
| 16 | n-$C_5H_{11}$ | $CH_3$ | 59-60 (EtOH) | Pale yellow needles | NaH/DMF | 69.8 |
| 17 | n-$C_6H_{13}$ | $C_2H_5$ | 56-57 (EtOH) | Pale yellow needles | NaH/DMF | 75.7 |
| 18 | n-$C_7H_{15}$ | $C_2H_5$ | 60-63 (EtOH) | Pale yellow needles | NaH/DMF | 82.5 |
| 19 | n-$C_8H_{17}$ | $C_2H_5$ | 50-52 (EtOH) | Pale yellow plates | NaOH/acetone | 75.6 |
| 20 | n-$C_{10}H_{21}$ | $C_2H_5$ | 46-47 (EtOH) | Pale yellow powder | NaH/DMF | 83.8 |
| 21 | sec-$C_4H_9$ | $C_2H_5$ | 72-73 (EtOH) | Pale yellow paltes | KOH/acetone | 74.4 |
| 22 | cyclo-$C_6H_{11}$ | $C_2H_5$ | 74-76 (EtOH) | Pale yellow needles | KOH/acetone | 68.3 |

Example 23

Preparation of 2'-carboxymethoxy-4-n-hexyl-4'-(3-methyl-2-butenyloxy)chalcone

To a solution of 4.30 g of 2'-ethoxycarbonylmethoxy-4-n-hexyl-4'-(3-methyl-2-butenyloxy)chalcone in 43 ml of ethanol was added a solution of 6.2 g of potassium carbonate in 11 ml of water, and the mixture was stirred at 50° C. for 5 hours. After completion of the reaction, the mixture was neutralized with dilute hydrochloric acid, and the precipitated solid was collected by filtration, washed with water, dried and recrystallized from ethyl acetate-n-hexane to give 3.13 g of 2'-carboxymethoxy-4-n-hexyl-4'-(3-methyl-2-butenyloxy)chalcone. m.p. 106°-108° C.

MS m/z: 450(M+), 69

IR$\nu_{max}^{KBR}$ cm$^{-1}$: 3429(COCH), 2928, 2858, 1741(C=O), 1647(C=O), 1607, 1578, 1249, 1023.

PMR (DMSO-d$_6$) δ: 0.87(3H, t, J=7 Hz), 1.20-1.32(6H, m), 1.51-1.70(2H, m), 1.75(3H, s), 1.77(3H, s), 2.61(2H, t, J=7 Hz), 4.63(2H, d, J=7 Hz), 4.92(2H, s), 5.45(1H, t, J=7 Hz), 6.65-6.70(2H, m), 7.24(2H, d, J=8 Hz), 7.60(1H, J=16 Hz), 7.68(1H, d, J=9 Hz), 7.69(2H, d, J=8 Hz), 7.97(1H, d, J=16 Hz), 13.28(1H, s).

Examples 24 to 36

In a similar manner to that of Example 23, the compounds shown in Table 3 were obtained.

TABLE 3

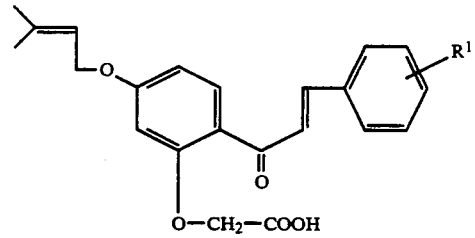

| Example | $R^1$ and the position | m.p. (°C.) | Appearance | Hydrolysis conditions | Yield (%) |
|---|---|---|---|---|---|
| 24 | sec-$C_4H_9$, 4 | 127-130 | Pale yellow powder | aq$K_2CO_3$/EtOH, 60° C. | 73.2 |
| 25 | n-$C_4H_9$, 4 | 119-121 | Pale yellow needles | aq$K_2CO_3$/MeOH, 60° C. | 74.3 |
| 26 | iso-$C_4H_9$, 4 | 150-153 | Pale yellow plates | aqKOH/EtOH, 25° C. | 73.5 |
| 27 | n-$C_5H_{11}$, 4 | 125-126 | Pale yellow needles | aq$Na_2CO_3$/EtOH, 60° C. | 75.0 |
| 28 | iso-$C_5H_{11}$, 4 | 123-124 | Pale yellow needles | aq$K_2CO_3$/EtOH, 50° C. | 82.3 |
| 29 | n-$C_6H_{13}$, 4 | 106-108 | Pale yellow needles* | aq$K_2CO_3$/EtOH, 50° C. | 77.2 |
| 30 | n-$C_7H_{15}$, 4 | 105-107 | Pale yellow needles | aq$K_2CO_3$/EtOH, 60° C. | 85.6 |
| 31 | n-$C_8H_{17}$, 4 | 92-94 | Pale yellow needles | aq$K_2CO_3$/EtOH, 45° C. | 68.2 |
| 32 | n-$C_{10}H_{21}$, 4 | 90-92 | Pale yellow powder | aqKOH/EtOH, 25° C. | 76.8 |
| 33 | n-$C_{15}H_{31}$, 4 | 82-84 | Pale yellow needles** | aq$K_2CO_3$/EtOH, 40° C. | 76.3 |
| 34 | cyclo-$C_6H_{11}$, 4 | 141-143 | Pale yellow powder | aq$K_2CO_3$/EtOH, 45° C. | 66.3 |
| 35 | n-$C_7H_{15}$, 2 | 118-121 | Pale yellow plates | aq$K_2CO_3$/EtOH, 50° C. | 76.3 |

TABLE 3-continued

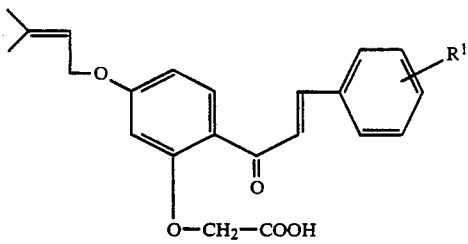

| Example | R¹ and the position | m.p. (°C.) | Appearance | Hydrolysis conditions | Yield (%) |
|---|---|---|---|---|---|
| 36 | n-$C_{15}H_{31}$, 2 | 82–83 | Pale yellow powder | aq$K_2CO_3$/EtOH, 40° C. | 62.4 |

(Note)
all case, solvents for recrystallization were ethanol except ethyl acetate in sign * and ether - n-hexane in sign **

Example 37

Preparation of 2-n-heptyl-2'-hydroxy-4'-(3-methyl-2-butenyloxy)chalcone (1) To a solution of 87.7 g of n-heptylbenzene in a mixture of 160 ml of nitroethane and 480 ml of dichloroethane was added little by little 79.5 g of anhydrous aluminum chloride with ice cooling, followed by adding dropwise a solution of 54.5 ml. of dichloromethyl methyl ether in 60 ml of dichloroethane. After completion of the addition, the reaction was carried out at 0° C. for a further one hour. The reaction mixture was poured into ice water and extracted with chloroform. The organic layer was washed with water and dried, and the solvent was evaporated. The residue was chromatographed on silica gel column with a solvent of n-hexane - isopropyl ether (10:1) to give 17.3 g of 2-heptylbenzaldehyde as a colorless oil from the first eluted fractions and 64.8 g of 4-heptylbenzaldehyde as a colorless oil from the later eluted fractions.

(2) To a solution of 3.11 g of 2-heptylbenzaldehyde and 3.35 g of 2'-hydroxy-4'-(3-methyl-2-butenyloxy)-acetophenone in 65 ml of isopropanol was added a solution of 2.9 g of sodium hydroxide in 6 ml of water under a nitrogen atmosphere, and the mixture was stirred at 45° C. for 8 hours. After neutralization with dilute hydrochloric acid with ice cooling, the mixture was extracted with ethyl acetate. The organic layer was washed with water and dried, and the solvent was evaporated under reduced pressure. The residue was purified by silica gel column chromatography with n-hexane including 1% ethyl acetate. The resulting fractions containing the end compound was recrystallized from isopropanol to give 3.23 g of 2-n-heptyl-2'-hydroxy-4'-(3-methyl-2-butenyloxy)-chalcone as yellow needles.
m.p. 65°–67° C.

Example 38

Preparation of 2'-carboxymethoxy-2-n-heptyl-4'-(3-methyl-2-butenyloxy)chalcone

To a suspension of 310 mg of 60% oily sodium hydride in 10 ml of dry DMF was added dropwise a solution of 2.8 g of 2-n-heptyl-2'-hydroxy-4'-(3-methyl-2-butenyloxy)chalcone in 10 ml of DMF with ice cooling. Then, 1.2 g of ethyl bromoacetate was added, and the mixture was stirred at room temperature for an hour. After neutralization with dilute hydrochloric acid, the mixture was extracted with ethyl acetate. The organic layer was washed with water and dried, and the solvent was evaporated under reduced pressure. The residue was chromatographed on silica gel column with n-hexane containing 1% ethyl acetate to give 1.83 g of 2'-ethoxycarbonylmethoxy-2-n-heptyl-4'-(3-methyl-2-butenyloxy)-chalcone. To a solution of this compound in 30 ml of ethanol was added 15 ml of 10% aqueous potassium carbonate solution, and the mixture was stirred at 60° C. for 4.5 hours. After neutralization with dilute hydrochloric acid with ice cooling, the precipitated solid was collected by filtration and recrystallized from ethanol to give 1.23 g of 2'-carboxymethoxy-2-n-heptyl-4'-(3-methyl-2-butenyloxy)chalcone as pale yellow plates.
m.p. 118°–121° C.
MS m/z: 464(M+), 297, 69
IR$\nu_{max}^{KBr}$ cm$^{-1}$: 3430(COOH), 2922, 2857, 1759(C=O), 1632(C=O), 1605, 1570, 1543.
PMR (DMSO-$d_6$) 6: 0.85(3H, t, J=7 Hz), 1.24–1.29(8H, m), 1.51(2H, brs), 1.74(3H, s), 1.76(3H, s), 2.74(2H, t, J=7 Hz), 4.62(2H, d, J=6 Hz), 4.92(2H, s), 5.44(1H, t, J=6 Hz), 6.66–6.71(2H, m), 7.19–7.37(3H, m), 7.67(1H, d, J=9 Hz), 7.87–7.91(3H, m), 13.28(1H, s).

Example 39

Preparation of 2'-carboxymethoxy-4-n-heptyl-4'-(3-methyl-2-butenyloxy)chalcone

To a solution of 3.48 9 of 2'-carboxymethoxy-4'-(3-methyl-2-butenyloxy)acetophenone and 2.80 g of 4-n-heptylbenzaldehyde in 120 ml of ethanol was added 3.5 g of potassium hydroxide, and the mixture was stirred for 5 hours. After neutralization with dilute sulfuric acid, the resulting precipitate was collected by filtration, washed with water, dried and recrystallized from ethanol to give 4.10 g of 2'-carboxymethoxy-4-n-heptyl-4'-(3-methyl-2-butenyloxy)chalcone as pale yellow needles.
m.p. 106°–107° C.
MS m/z: 464(M+), 189, 69
IR$\nu_{max}^{KBr}$ cm$^{-1}$: 3467(COOH), 2955, 2922, 1740(C=O), 1645(C=O), 1604, 1498, 1422, 1252, 1183.
PMR (DMSO-$d_6$) 6: 0.85(3H, t, J=7 Hz), 1.19–1.27(8H, m), 1.57(2H, m), 1.73(3H, s), 1.76(3H, s), 2.60(2H, t, J=7 Hz), 4.62(2H, d, J=7 Hz), 4.90(2H, s), 5.44(1H, t, J=7 Hz), 6.64–6.69(2H, m), 7.23(2H, d, J=8 Hz), 7.59(1H, d, J=16 Hz), 7.67(1H, d, J=9 Hz), 7.68(2H, d, J=8 Hz), 7.96(1H, d, J=16 Hz), 13.27(1H, s).

Examples 40 and 41

In a similar manner to that of Example 39, the compounds shown in Table 4 were obtained.

TABLE 4

[Structure: chalcone with prenyloxy group at 4'-position, O—CH₂—COOH at 2'-position, and R¹ at 4-position]

| Example | R¹ | m.p. (°C.) | Appearance (Solvent for recrystallization) | Yield (%) |
|---|---|---|---|---|
| 40 | n-C₆H₁₃ | 106–108 | Pale yellow needles (ethanol) | 78.4 |
| 41 | t-C₄H₉ | 137–140 | Pale yellow needles (isopropanol-n-hexane) | 65.6 |

Example 42

Preparation of 4-t-butyl-2'-hydroxy-4'-(3-methyl-2-butenyloxy)chalcone

To a solution of 54.4 g of 2'-hydroxy-4'-(3-methyl-2-butenyloxy)acetophenone and 40.0 g of 4-t-butylbenzaldehyde in 1000 ml of ethanol was added 81.2 g of potassium hydroxide, and the mixture was stirred at 40° C. for 19 hours. After neutralization with dilute hydrochloric acid, the resulting precipitate was collected by filtration, washed with water, dried and recrystallized from isopropanol to give 47.6 g of 4-t-butyl-2'-hydroxy-4'-(3-methyl-2-butenyloxy)chalcone as a yellow powder.

Example 43

Preparation of 4-t-butyl-2'-ethoxycarbonylmethoxy-4'-(3-methyl-2-butenyloxy)chalcone To a solution of 45.1 g of 4-t-butyl-2'-hydroxy-4'-(3-methyl-2-butenyloxy)chalcone in 500 ml of acetone was added 10.6 g of potassium hydroxide, and the mixture was stirred for 5 minutes. Then, 21.5 g of ethyl bromoacetate was added, and the mixture was stirred for 45 minutes. After neutralization with dilute hydrochloric acid, the precipitated solid was collected by filtration, washed with water, dried and recrystallized from ethanol to give 47.6 g of 4-t-butyl-2'-ethoxycarbonylmethoxy-4'-(3-methyl-2-butenyloxy)chalcone as a pale yellow powder.
m.p. 78°–79° C.

Example 44

Preparation of 4-t-butyl-2'-carboxymethoxy-4'-(3-methyl-2-butenyloxy)chalcone To a solution of 47.3 g of 4-t-butyl-2'-ethoxycarbonylmethoxy-4'-(3-methyl-2-butenyloxy)chalcone in 600 ml of ethanol was added a solution of 29.0 g of potassium carbonate in 100 ml of water, the mixture was stirred at 45° C. for 8 hours. After neutralization with dilute sulfuric acid, the precipitated solid was collected by filtration, washed with water, dried and recrystallized from ethanol to give 29.9 g of 4-t-butyl-2'-carboxymethoxy-4'-(3-methyl-2-butenyloxy)chalcone as pale yellow needles.
m.p. 136°–139° C.
IR$\nu_{max}^{KBr}$ cm$^{-1}$: 3430(COOH), 2963, 1753(C=O), 1645(C=O), 1615, 1579, 1177.
PMR (CDCl₃) δ: 1.35(9H, s), 1.78(3H, s), 1.83(3H, s), 4.60(2H, d, J=7 Hz), 4.79(2H, s), 5.48(1H, t, J=7 Hz), 6.57(1H, d, J=2 Hz), 6.68(1H, dd, J=9 Hz, 2 Hz), 7.31(1H, d, J=16 Hz), 7.45(2H, d, J=9 Hz), 7,58(2H, d, J=9 Hz), 7.75(1H, d, J=9 Hz), 7.81(1H, d, J=16 Hz)

Example 45

Preparation of 4-(t-butyl)-2'-(1-carboxethoxy)-4'-(3-methyl-2-butenyloxy)chalcone (1) To a suspension of 4.0 g of sodium hydride in 40 ml of dimethylformamide was added dropwise a solution of 22.0 g of 2'-hydroxy-4'-(3-methyl-2-butenyloxy)acetophenone in 10 ml of dimethylformamide. Then, a solution of 18.5 g of ethyl 2-bromopropionate in 10 ml of dimethylformamide was added dropwise, and the mixture was stirred at room temperature for 3 hours and neutralized with dilute hydrochloric acid. The mixture was extracted with ethyl acetate, and the organic layer was washed with water and dried. The solvent was evaporated to give 31.6 g of an oil, which was then dissolved in 320 ml of ethanol. To the resulting solution was added 35 ml of an aqueous solution of 40 g of potassium carbonate, and the mixture was stirred at 70° C. for 7 hours. After neutralization with dilute hydrochloric acid, the mixture was extracted with ethyl acetate. The organic layer was washed with water and dried, and the solvent was evaporated under reduced pressure. The residue was recrystallized from isopropyl ether to give 19.7 g of 2'-(1-carboxyethoxy)-4'-(3-methyl-2-butenyloxy)acetophenone as a white powder.

(2) To a solution of 1.1 g of 2'-(1-carboxyethoxy)-4'-(3-methyl-2-butenyloxy)acetophenone and 0.62 g of 4-(t-butyl)benzaldehyde in 20 ml of ethanol was added 0.84 g of potassium hydroxide, and the mixture was stirred for 45 minutes. After neutralization with dilute hydrochloric acid, the mixture was extracted with ethyl acetate. The organic layer was washed with water and dried, the solvent was evaporated under reduced pressure, and the residue was chromatographed on silica gel column with n-hexane - ethyl acetate (10:1) and recrystallized from benzene - n-hexane to give 0.91 g of the title compound as a pale yellow powder.
m.p. 119°–122° C.

Examples 46 to 48

In a similar manner to that of Example 45, the compounds shown in Table 5 were obtained.

TABLE 5

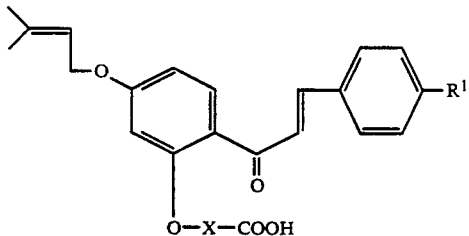

| Example | R¹ | —X— | m.p. (°C.) (Solvent for recrystallization) | Appearance | Yield (%) in condensation |
|---|---|---|---|---|---|
| 46 | n-$C_6H_{13}$ | —CH—<br>\|<br>$CH_3$ | 93–95<br>(IPE-n-hexane) | Pale yellow powder | 61.3 |
| 47 | t-$C_4H_9$ | —C—<br>/ \<br>$CH_3$  $CH_3$ | | Pale yellow glasses | 47.5 |
| 48 | t-$C_4H_9$ | —$(CH_2)_3$— | 131–132<br>(ethyl acetate-n-hexane) | Pale yellow needles | 58.3 |

Example 49

Preparation of 2'-carboxymethoxy-4'-(3-methyl-2-butenyloxy)-4-(1-(E)-octenyl)chalcone (1) To a solution of 15.7 g of terephthalaldehyde and 51.6 g of n-heptyltriphenylphosphonium bromide in 136 ml of dioxane was added 2.7 g of water followed by 32.3 g of potassium carbonate, and the mixture was vigorously stirred under reflux. After 10 hours, n-hexane was added to the cooled reaction mixture. The precipitated crystals were removed by filtration, and the solvent was evaporated under reduced pressure. The remaining oil was chromatographed on silica gel column with n-hexane containing 5% isopropyl ether to 21.9 g of 4-(1-octenyl)benzaldehyde as an oil.

(2) To a solution of 9.35 g of 2'-carboxymethoxy-4'-(3-methyl-butenyloxy)acetophenone and 7.37 g of 4-(1-octenyl)benzaldehyde in 170 ml of ethanol was added 11.5 g of potassium hydroxide and the mixture was stirred for 45 minutes. After neutralization with dilute hydrochloric acid, the precipitated solid was collected by filtration and recrystallized from 90% ethanol to give 9.2 g of 2'-carboxymethoxy-4'-(3-methyl-2-butenyloxy)-4-(1-(E)-octenyl)chalcone of the title compound as a plae yellow powder.

m.p. 103°–105° C.

MS m/z: 476 (M+) 69

$IR\nu_{max}^{KBr}$ cm$^{-1}$: 3432(COOH), 2925, 1746(C=O), 1646(C=O),

PMR (DMSO-$d_6$) δ: 0.87(3H, t, J=7 Hz), 1.22–1.52(8H, m), 1.73(3H, d, J=1Hz), 1.76(3H, s), 2.14–2.28(2H, m),, 4.62(2H, d, J=7 Hz), 4.91(2H, s), 5.40–5.50(1H, m), 6.39–6.44(2H, m), 6.64–6.70(2H, m), 7.42(2H, d, J=8 Hz), 7.59(1H, d, J=16 Hz), 7.68(1H, d, J=8 Hz), 7.71(2H, d, J=8 Hz). 7.98(1H, d, J=16 Hz), 13.26(1H, s),

Examples 50 to 52

In a similar manner to that of Example 49, the compounds shown in Table 6 were obtained.

TABLE 6

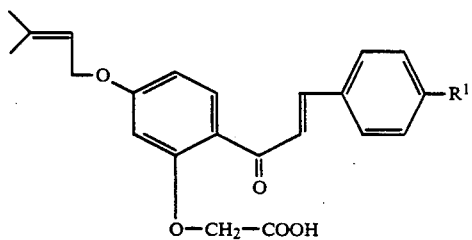

| Example | R¹ | m.p. (°C.), Appearance (Solvent for recrystallization) | Yield (%) in condensation |
|---|---|---|---|
| 50 | 1-(E)-pentenyl | 127–130, Pale yellow powder (ethanol-water) | 53.8 |
| 51 | 1-(E)-hexanyl | 121–123, Pale yellow powder (ethanol-water) | 62.7 |
| 52 | 1-(E)-heptenyl | 116–118, Pale yellow powder (ethanol-water) | 51.3 |

Example 53

Preparation of 2-(1-carboxymethoxy)-4'-(3-methyl-2-butenyloxy)-4-(4-pentenyl)chalcone (1) To a suspension of 970 mg of magnesium in 20 ml of tetrahydrofuran was added dropwise a solution of 5.4 g of 4-bromo-1-butene in 20 ml of tetrahydrofuran while keeping at 50° C. Then, a solution of 10.0 g of 4-bromobenzyl bromide in 20 ml of tetrahydrofuran was added dropwise slowly, and the mixture was refluxed for an hour, made acidic with dilute hydrochloric acid and extracted with n-hexane. The organic layer was washed with water and dried over magnesium sulfate. The solvent was evaporated under reduced pressure, and the residue was chromatographed on silica gel column with n-hexane to give 1.14 g of 4-(4-pentenyl)bromobenzene.

(2) To a solution of 1.13 g of 4-(4-pentenyl)-bromobenzene in 20 ml of tetrahydrofuran wa added dropwise 4 ml of 1.5 M n-butyl lithium in n-hexane with dry-ice - acetone cooling, and the mixture was stirred for 15 minutes. To the reaction mixture was added 0.58 ml of dimethylformamide and stirred for an hour. Then the reaction mixture, after addition of 50 ml of water, was extracted with ether. The organic layer was washed with water and dried. Evaporation of the solvent under reduced pressure gave 850 mg of 4-(4-pentenyl)benzaldehyde.

(3) To a solution of 1.12 g of 2'-(1-carboxymethoxy)-4'-(3-methyl-2-butenyloxy)acetophenone and 850 mg of 4-(4-pentenyl)benzaldehyde in 15 ml of isopropyl alcohol was added 670 mg of potassium hydroxide, and the mixture was stirred for 15 minutes. After neutralization with dilute hydrochloric acid, the mixture was extracted with ethyl acetate. The organic layer was washed with water and dried, and the solvent was evaporated under reduced pressure. The residue was recrystallized from ethyl acetate - n-hexane to give 920 mg of the title compound as a pale yellow powder.

m.p. 116°–118° C.

Examples 54–56

In a similar manner to that of Example 43, the compounds shown in Table 7 were obtained.

TABLE 7

| Example | $R^1$ | m.p. (°C.), Appearance (Solvent for recrystallization) | Yield (%) in condensation |
|---|---|---|---|
| 54 | 3-butenyl | 111–112, Pale yellow needles (ethyl acetate-n-hexane) | 49.8 |
| 55 | 5-hexenyl | 109–110, pale yellow powder (ethyl acetate-n-hexane) | 53.2 |
| 56 | 6-heptenyl | 96–97, Pale yellow powder (ethyl acetate-n-hexane) | 57.1 |

Example 57

Preparation of 2'-(carboxymethoxy)-4'-(3-methyl-2-butenyloxy)-4-(2-propenyl)chalcone (1) A solution of 27.75 g of 4-bromobenzaldehyde, 12 g of ethyleneglycol and catalytic amount of p-toluenesulfonic acid in benzene was refluxed for 2 hours using a water separator. The solvent was evaporated under reduced pressure, and the residue was distilled under reduced pressure to give 27.9 g of 2-(4-bromophenyl)-1,3-dioxorane.

(2) To a suspension of 486 mg of magnesium in 20 ml of tetrahydrofuran was added dropwise a solution of 4.58 g of 2-(4-bromophenyl)-1,3-dioxorane in 40 ml of tetrahydrofuran while keeping at 50° C. Then, a solution of 4.84 g of allyl bromide in 20 ml of tetrahydrofuran was added dropwise slowly, and the mixture was refluxed for an hour, treated with dilute hydrochloric acid and extracted with ether. The organic layer was washed successively with water and brine, and dried over magnesium sulfate. The solvent was evaporated under reduced pressure, and the residue was chromatographed on silica gel column with ether - n-hexane (1:100) to give 900 mg of 4-(2-propenyl)benzaldehyde.

(3) To a solution of 834 mg of 2'-(1-carboxymethoxy)-4'-(3-methyl-2-butenyloxy)acetophenone and 500 mg of 4-(2-propenyl)benzaldehyde in 10 ml of ethanol was added 842 mg of potassium hydroxide, and the mixture was stirred for 20 minutes. After neutralization with dilute hydrochloric acid, the mixture was extracted with ethyl acetate. The organic layer was washed with water and dried, and the solvent was evaporated under reduced pressure. The residue was recrystallized from ethyl acetate - n-hexane to give 360 mg of the title compound as a pale yellow needles.

m.p. 125°–126° C.

Experiment 1 Stress Ulcer Inhibition Test

Test drug

The test drugs used were the compounds obtained in the foregoing Examples. Number in test drug column of Table 8 means a compound which is prepared in the correspondingly numbered Example.

Also, symbols A–E in test drug column of Table 8 mean the following compounds used as the control compounds.

A: 4-carboxy-2'-carboxymethoxy-4'-(3-methyl-2-butenyloxy)chalcone

B: 2',4-bis(carboxymethoxy)-4'-(3-methyl-2-butenyloxy)chalcone

C: 2'-carboxymethoxy-4,4'-bis(3-methyl-2-butenyloxy)chalcone

D: 2'-carboxymethoxy-4-methyl-4'-(3-methyl-2-butenyloxy)chalcone

E: 2'-carboxymethoxy-4'-(3-methyl-2-butenyloxy)-4-n-propylchalcone

Test Method

The stress ulcer inhibition test was carried out according to a method of K. Takagi et al as described in Japan J. Pharmacol., vol. 18, page 9 (1968).

Male Wistar rats weighing 160 to 180 g (7 animals for each group), after a 24 hour-fast, were given orally the test drug (50 mg/kg and/or 100 mg/kg) suspended in 0.4% CMC, and placed in the stress cage made of a galvanized wire net, which was then immersed into the thermostatic water bath kept on 23° C. until the lower part of the sternum of the animals. Seven hours later, the animals were lapotomized to measure the area of the mucosa produced in the stomach, and the inhibition ration was calculated.

Result

Results are shown in Table 8.

TABLE 8

| Test drug | Inhibition ratio (%) | |
|---|---|---|
| | 100 mg/kg | 50 mg/kg |
| 24 | | 70.5 |
| 25 | 63.0 | 61.0 |
| 27 | | 86.3 |
| 28 | | 89.0 |
| 29 | | 67.3 |
| 30 | | 91.8 |
| 31 | | 77.2 |
| 36 | | 48.7 |
| 44 | 84.2 | 76.0 |
| 45 | | 50.4 |
| 46 | | 63.0 |
| 48 | 72.0 | |
| 49 | | 76.6 |
| 51 | | 93.3 |
| 52 | | 93.4 |
| 54 | | 56.9 |
| A | | <10 |
| B | | <10 |
| C | | <10 |
| D | 26.2 | <10 |
| E | 57.1 | 33.7 |

Experiment 2 Gastric Mucosal Protection Test

Test drug

The test drugs used were the compounds obtained in the foregoing Examples. Number in test drug column of Table 8 means a compound which is prepared in the correspondingly numbered Example.

Also, symbols A-E in test drug column of Table 9 are as defined in Experiment 1.

Test Method

The test of protection effect against the gastric lesions induced by 0.6 N hydrochloric acid (gastric mucosal protection effect) was carried out according to a method of A. Robert et al as described in Gastroenterology, vol. 77, pages 433–443 (1979).

Male Wistar rats weighing 180–210 g (7 animals for each group), after a 24 hour-fast, were given orally the test drug (50 mg/kg and/or 100 mg/kg) suspended in 0.4% CMC. After standing at room temperature for 2 hours, 0.6 N hydrochloric acid was given orally in a dose of 1 ml per rat. After standing at room temperature for a further one hour, rats were killed to measure the length of the gastric mucosal lesions induced in the stomachs, and total of the length was designated as the lesion index per rat.

The inhibition ratio (%) was calculated by comparison of the lesion index of the group treated with the test drug with the untreated group.

Result

Results are shown in Table 9.

TABLE 9

| Test drug | Inhibition ratio (%) | |
|---|---|---|
| | 100 mg/kg | 50 mg/kg |
| 18 | 53.8 | 37.6 |
| 29 | 83.7 | 81.2 |
| 30 | 94.4 | 83.8 |
| 44 | 82.8 | 61.9 |
| A | | <10 |
| B | | <10 |
| C | | <10 |
| D | | <10 |

TABLE 9-continued

| Test drug | Inhibition ratio (%) | |
|---|---|---|
| | 100 mg/kg | 50 mg/kg |
| E | | 24.8 |

Experiment 3  2-DG-induced Acid Secretion Test Gastric Lumen Perfused Rats

The test was carried out according to the method of K. Watanabe et al in Eur. J. Pharmacology, vol. 90, page 11–17 (1983), and the inhibition ratio of gastric acid secretion of the test drug was calculated. Results were shown in Table 10.

TABLE 10

| Test drug | Dose (mg/kg) | Inhibition ratio (%) |
|---|---|---|
| 44 | 100 | 66.8 |
| 44 | 30 | 54.3 |
| C | 200 | 35.2 |

(Note)
Number and symbol in test drug column are as defined above.

The test drug was given intraperitoneally.

What is claimed is:

1. A chalcone derivative represented by the formula

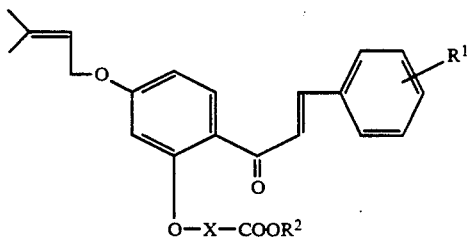

wherein $R^1$ is a straight chain, branched chain or cyclic alkyl group having 4 to 15 carbon atoms or an alkenyl group having 3 to 15 carbon atoms, and occurs at the 2- or 4-position, $R^2$ is a hydrogen atom, or a straight or branched chain alkyl group having 1 to 3 carbon atoms, and X is a straight or branched chain alkylene group having 1 to 3 carbon atoms.

2. A chalcone derivative according to claim 1 wherein $R^1$ is a straight chain alkyl group having 5 to 8 carbon atoms, a branched chain alkyl group having 4 to 7 carbon atoms or an alkenyl group having 4 to 8 carbon atoms, $R^2$ is a hydrogen atoms or a straight or branched chain alkyl group having 1 to 3 carbon atoms, and X is a methylene group.

3. A chalcone derivative according to claim 1 wherein $R^1$ is a straight chain alkyl group having 6 or 7 carbon atoms, a branched chain alkyl group having 4 carbon atoms or a 1-alkenyl group having 6 or 7 carbon atoms, and occurs at the 4-position, $R^2$ is a hydrogen atoms, and X is a methylene group.

4. 2'-Carboxymethoxy-4-hexyl-4'-(3-methyl-2-butenyloxy)chalcone.

5. 2'-Carboxymethoxy-4-heptyl-4'-(3-methyl-2-butenyloxy)chalcone.

6. 2'-Carboxymethoxy-4-(1-(E)-hexenyl)-4'-(3-methyl-2-butenyloxy)chalcone.

7. 2'-Carboxymethoxy-4-(1-(E)-heptenyl)-4'-(3-methyl-2-butenyloxy)chalcone.

8. 4-t-Butyl-2'-carboxymethoxy-4'-(3-methyl-2-butenyloxy)chalcone.

* * * * *

UNITED STATES PATENT AND TRADEMARK OFFICE
CERTIFICATE OF CORRECTION

PATENT NO. : 5,089,654
DATED : February 18, 1992
INVENTOR(S) : YOKOMORI et al

Page 1 of 2

It is certified that error appears in the above-identified patent and that said Letters Patent is hereby corrected as shown below:

Column 6, line 4, delete "7".

Column 7, line 30, in TABLE 2, under "Appearance", Example 21, "pale yellow paltes" should read --pale yellow plates--.

Column 8, line 6, "(COCH)," should read --(COOH)--.

Column 10, line 38, "6:" should read --$\delta$:--; and
line 64, "6:" should read --$\delta$:--.

Column 12, line 28, "carboxethoxy" should read --carboxyethoxy--.

Column 14, line 55, "2" should read --2'--.

UNITED STATES PATENT AND TRADEMARK OFFICE
CERTIFICATE OF CORRECTION

PATENT NO.  : 5,089,654
DATED       : February 18, 1992
INVENTOR(S) : YOKOMORI et al It is certified that error appears in the above-identified patent and that said Letters Patent is hereby corrected as shown below:

Column 18, line 23, "The test drug was given intraperitoneally." should be included under "(Note)"

Signed and Sealed this

Twenty-fifth Day of May, 1993

Attest:

MICHAEL K. KIRK

Attesting Officer

Acting Commissioner of Patents and Trademarks